United States Patent [19]

Kaffka et al.

[11] Patent Number: 4,566,797
[45] Date of Patent: Jan. 28, 1986

[54] SPECTROPHOTOMETER OPERATING AT DISCRETE WAVELENGTHS

[75] Inventors: Károly Kaffka; Béla Nádai; András Czabaffy; Loránd Horváth, all of Budapest, Hungary

[73] Assignee: Kozponti Elelmiszeripari Kutato Intezet, Budapest, Hungary

[21] Appl. No.: 502,734

[22] Filed: Jun. 9, 1983

[30] Foreign Application Priority Data

Jun. 9, 1982 [HU] Hungary .............................. 1869/82

[51] Int. Cl.$^4$ .............................................. G01J 3/42
[52] U.S. Cl. ..................................... 356/402; 356/420
[58] Field of Search ................... 356/319, 323–325, 356/73, 402, 409–411, 414, 420, 425, 432–439

[56] References Cited

U.S. PATENT DOCUMENTS

| | | | |
|---|---|---|---|
| 3,523,748 | 8/1970 | Chisholm et al. | 431/264 |
| 3,910,701 | 10/1975 | Henderson et al. | 356/73 X |
| 3,935,463 | 1/1976 | Jacobsen | 250/373 |
| 3,994,590 | 11/1976 | Di Martini et al. | 356/409 X |
| 4,011,009 | 3/1977 | Lama et al. | |
| 4,105,333 | 8/1978 | Kaule et al. | 250/365 |
| 4,305,664 | 12/1981 | Akitomo | 356/323 |

FOREIGN PATENT DOCUMENTS

2116386 10/1972 Fed. Rep. of Germany ...... 356/420

OTHER PUBLICATIONS

Bausch & Lomb Brochure–Atomic Absorption.

*Primary Examiner*—F. L. Evans
*Attorney, Agent, or Firm*—Young & Thompson

[57] ABSTRACT

The invention relates to a spectrophotometer operating at discrete wavelengths comprising diodes to emit variable, substantially monochromatic radiation for irradiating a sample (10) to be tested, a radiation detector (12) sensing the intensity of the radiation reflected or transmitted by the sample (10) and a signal processing unit connected to the radiation detector (12). The diodes comprise radiation sources (2) emitting substantially monochromatic radiation of different wavelengths, a holder (1) supporting the radiation sources (2) and an optical arrangement (5,6) for transmitting the radiation emitted by the radiation sources (2) successively towards the sample (10). The optical arrangement may comprise at least one mirror (5) supported rotatably with respect to the holder (1). The spectrophotometer is preferably provided with a control unit (3) to operate the radiation sources (2) corresponding to the angular position of said at least one mirror (5), whereby only that one of the radiation sources (2) is operating the radiation of which is just transmitted by the mirror (5).

7 Claims, 1 Drawing Figure

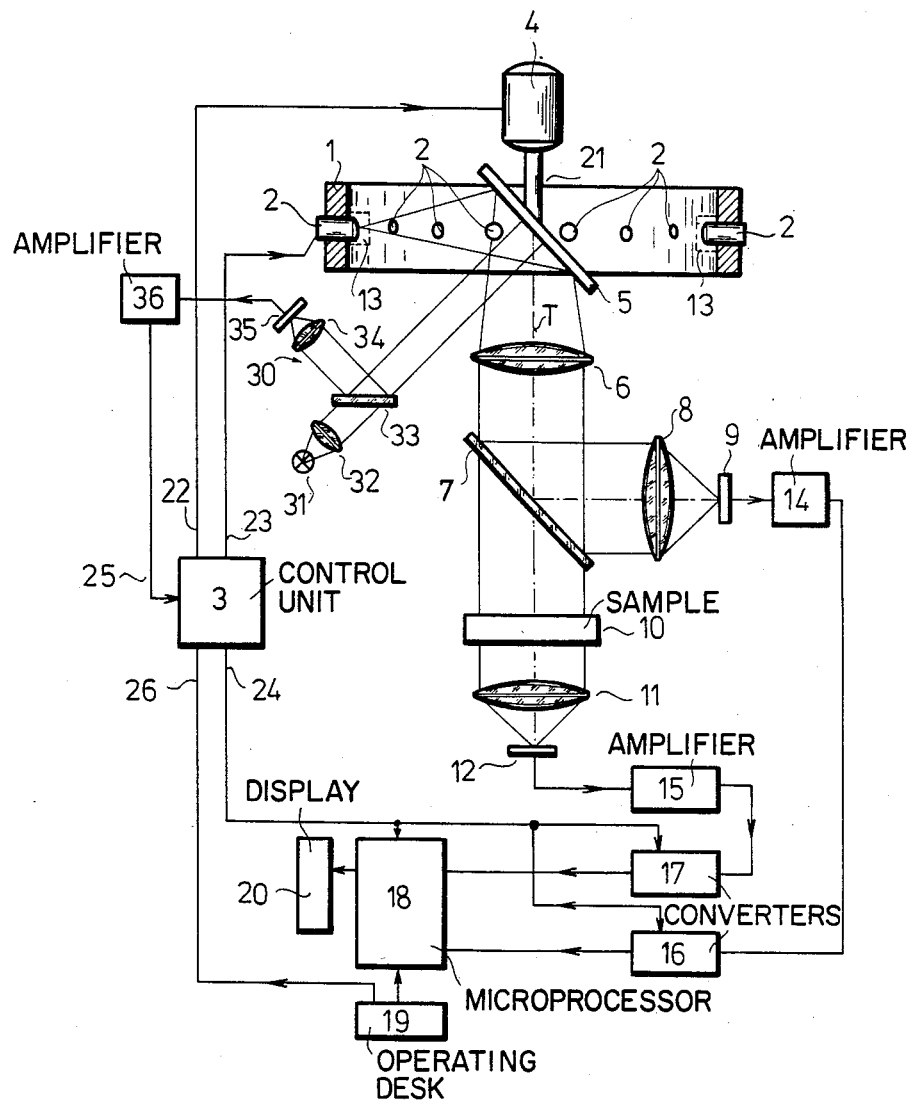

SPECTROPHOTOMETER OPERATING AT DISCRETE WAVELENGTHS

TECHNICAL FIELD

The subject matter of the present invention is a spectrophotometer operating at discrete wavelengths.

BACKGROUND ART

Spectrophotometers have already been known which are suitable to determine the transmission or reflection spectrum of different samples at a number of discrete wavelengths. In one of these spectrophotometers filters are turned before a broadband source, e.g. an incandescent lamp, whereby the light of the lamp is passed successively through different filters onto the sample to be tested, and the electronics connected to the detector sensing the light reflected or transmitted by the sample is synchronized with the turning of the filters. In this case the significant heat output of the lamp causes adverse warm up of the equipment. The thermosensitivity of the detectors and the interference filters in this particular case results in inaccuracy of measurements, and a thermal stability can only be attained a long time after switching on the equipment. In case of using interference filters a further measuring error is produced by the fact that, considering the total spectrum of the broadband source of radiation, the amount of the energy transmitted in the non-pass range of the interference filter is not negligible compared to the energy transmitted in the pass band. This is due to the fact that the bandwidth of the non-pass range is much higher than that of the pass-band.

DISCLOSURE OF THE INVENTION

The object of the present invention has been to create a spectrophotometer by which the measuring errors described above can be significantly decreased.

According to the invention this object can be achieved by applying several sources each emitting a substantially monochromatic radiation and an optical arrangement for transmitting these radiations successively towards the sample to be tested.

Hence the subject matter of the present invention is a spectrophotometer operating at discrete wavelengths comprising means to emit a variable, substantially monochromatic radiation for irradiating a sample to be tested, a radiation detector sensing the intensity of the radiation reflected or transmitted by the sample and a signal processing unit connected to the radiation detector. According to the invention said radiation emitting means comprises several radiation sources emitting substantially monochromatic radiations of different wavelengths, a holder for supporting the radiation sources and an optical arrangement for transmitting the radiation emitted by the radiation sources successively towards the sample.

In a preferred embodiment of the invention the optical arrangement comprises at least one mirror supported rotatably with respect to the holder.

In the spectrophotometer according to the invention the single sources of radiation are preferably solid state radiation emitting diodes or laser diodes. As each of these radiation sources emits in a narrow wavelength range only, the heat generated by the sources within the equipment is small and so the errors due to the temperature changes are also small. The heat generated in the spectrophotometer according to the present invention can be further decreased by switching on at any times that source of radiation only the radiation of which is just to be transmitted by said one or more mirrors. This can be accomplished by a control unit operating the radiation sources, being synchronized with the angular position of the mirror.

Said one or more mirrors may be rotated even by hand or, preferably, by a stepping motor or a conventional electric motor. In case of applying a stepping motor the spectrophotometer is provided with a transducer generating a signal in at least one angular position of said at least one mirror, the output of which being connected to the control unit, while one of the outputs of the control unit is connected to the control input of the stepping motor. The transducer provides for the synchronization between the status if the control unit and the angular position of the mirror. It is feasible to apply a transducer generating a signal in only one angular position, e.g. at the beginning of the spectrum, in which case the control unit has to be designed to generate as many stepping pulses or pulse series as the number of the discrete wavelengths is at which measurements are to be made. In case of an electric motor rotating the mirror continuously, a transducer providing a signal corresponding to the current angular position is connected to the control unit.

The signal processing unit connected to the radiation detector preferably comprises a first analog-to-digital converter connected to the output of the radiation detector via a first amplifier and a data processing unit connected to the output of the first analog-to-digital converter, wherein the control input of said first analog-to-digital converter is connected to an output of the control unit. The errors resulting from the time-dependent instability of the radiation sources can be eliminated by an embodiment comprising a beam splitter positioned in the path of the radiation beam before the sample, an additional radiation detector sensing the intensity of the radiation diverted by the beam splitter, and a second analog-to-digital converter connected to the output of said additional radiation detector via a second amplifier, wherein the control input of the second analog-to-digital converter is connected to control input of the first analog-to-digital converter, and the output of the second analog-to-digital converter is connected to the data processing unit. With this embodiment the data processing unit is programmed to calculate the ratio of the values measured at the same time by the first and the second analog-to-digital converters. An embodiment is preferred wherein the control unit and the data processing unit are realized by a microprocessor.

BRIEF DESCRIPTION OF THE DRAWING

The invention will be described in the following, on the basis of a preferred embodiment illustrated in the accompanying drawing showing a schematic view and block diagram of a spectrophotometer according to the invention.

MODES FOR CARRYING OUT THE INVENTION

In the drawing radiation sources 2, preferably solid state radiation emitting diodes or laser diodes, are mounted in a cylindrical holder 1. Each one of the radiation sources 2 emits a substantially monochromatic radiation at different wavelengths. The monochromatic feature of the radiation can be increased by filters 13 when required, for example by interference filters. The radiation sources 2 are successively operated by control signals from outputs 23 of a control unit 3. The radiation emitted by the radiation source 2 just operating is reflected by a mirror 5 onto a lens 6, said mirror 5 being supported rotatably by a shaft T. In the embodiment illustrated the mirror 5 is mounted on the shaft 21 of a motor 4, wherein the motor 4 and the holder 1 are fixed with respect to each other. The motor 4, being a stepping motor, is controlled with pulses or pulse series provided by the control unit 3 on its output 22, synchronized to the signals existing at the outputs 23 for operating the radiation sources 2. The beam of radiation reflected from mirror 5 towards the lens 6 passes through a splitter 7 to the sample 10. The radiation transmitted through the sample 10 is focused by a lens 11 onto a radiation detector 12, the output of which is connected to the analog input of an analog-to-digital converter 17 via an amplifier 15. The portion of the radiation reflected from the splitter 7 is focused by a lens 8 onto a radiation detector 9, the output of which is connected to the analog input of an analog-to-digital converter 16 via an amplifier 14. The control inputs of the analog-to-digital converters 16 and 17 are both connected to the output 24 of the control unit 3. The pulse starting the conversion appears on the output 24 at the moment when the radiation emitted by one of the radiation sources 2 is just projected by the mirror 5 on the sample 10.

The starting position of the mirror 5 is detected by the control unit 3 via a transducer 30 comprising a light source 31, a lens 32 projecting the light of the light source 31 onto the mirror 5 after passing through a beam splitter 33, e.g. a plano-parallel plate, and a lens 34 focusing the light reflected from the mirror 5 and the beam splitter 33 on a light detector 35. The output of the light detector 35 is connected to the input 25 of the control unit 3 via an amplifier 36. The transducer 30 transmits a signal to the control unit 3 in a single angular position of the rotating mirror 5. Following this the control unit 3 will generate as many pulses or pulse series as the number of the radiation sources 2 is, resulting in rotating the mirror 5 step by step by means of the stepper motor 4. The pulses starting the analog-to-digital conversions are generated by the control unit 3 on its output 24 corresponding to the pulses operating the radiation sources 2 successively, which are generated on the outputs 23.

The digital outputs of the analog-to-digital converters 16 and 17 are connected to a data processing unit 18 which is preferably a microprocessor, which receives also the pulses starting the analog-to-digital conversions on the output 24 of the control unit 3.

The data processing unit 18 computes the quotient of the signals measured simultaneously by the analog-to-digital converters 16 and 17 and this quotient is stored at each wavelength. The operator can access to the data processing unit 18 via an operating desk 19, and after the measurement the spectrum can be displayed on a display unit 20. The operating desk 19 is connected also to the starting input 26 of the control unit 3.

The spectrophotometer according to the present invention can also differ from the embodiment illustrated in the drawing. The radiation sources 2 may be mounted on a holder 1 different from that illustrated herein, it may be for example conical or annular. The essential feature is that the radiation sources 2 should be arranged so as to enable the scanning of them successively by an optical arrangement, e.g. by a rotating mirror system. If the radiation sources 2 are mounted on an annular holder for example so that they radiate upwards in the drawing, an additional mirror is to be attached to the mirror 5 to reflect the beam of radiation directed upwards onto the mirror 5, and both mirrors have to be rotated together for scanning the radiation sources 2. The radiation sources 2 may also be arranged to be scanned with a rotational reciprocating motion of a mirror system. A single rotatably supported concave mirror can also be used instead of the mirror 5 and the lens 6. The lens 6 can be omitted when the radiation sources 2 emit a parallel beam of radiation. The mirror 5 may also be rotated by a continuously rotating motor 4 instead of a stepping one, and in this case the transducer 30 is an angular position transducer mounted on the shaft 21 to provide a proper signal for the control unit 3 each time when scanning one of the radiation sources 2. It is also possible to rotate the pivoted mirror 5 manually in the course of the measurement, in which case there is no driving motor 4 at all. The transducer 30 sensing the angular position of the mirror 5 can be designed in many different ways, and various optical means e.g. angle reflector, chopper disc, electromechanical or magnetic (inductive) transducers or angular position decoders can be used.

The quotient may also be generated in a way different from that illustrated in the drawing, by means of an analog quotient meter for example connected to the outputs of the amplifiers 15 and 14, or a digital quotient meter connected to the outputs of the analog-to-digital converters 17 and 16. In a preferred embodiment the microprocessor constituting the data processing unit 18 serves also as a control unit 3. The spectrophotometer of the present invention is naturally applicable not only for transmission measurements as illustrated in the drawing but for reflection measurements, too.

We claim:

1. A spectrophotometer operating at discrete wavelengths comprising in combination
    several radiation emitting diodes emitting substantially monochromatic radiations of different wavelengths,
    a holder for supporting said diodes,
    an optical arrangement for transmitting the radiations emitted by said diodes towards a sample to be tested,
    means for changing the angular position of said optical arrangement thereby to transmit said radiation toward said sample successively,
    means for operating said diodes corresponding to the angular position of said optical arrangement and providing operational data about the diodes,
    a first radiation detector sensing the intensity of the radiation reflected or transmitted by the sample,
    a beam splitter positioned before the sample in the path of the radiation beam transmitted towards the sample,
    a second radiation detector sensing the intensity of the radiation diverted by the beam splitter,
    a first analog-to-digital converter to produce a digital signal corresponding to the signal of the first radiation detector,
    a second analog-to-digital converter to produce a digital signal corresponding to the signal of the second radiation detector,
    a data processing unit connected to the output of the first and second analog-to-digital converters, said unit computing spectrum data on the basis of the digital signals of said first and second analog-to-digital converters and said operational data.

2. The spectrophotometer according to claim 1, wherein said optical arrangement comprises at least one mirror supported rotatably with respect to said holder.

3. The spectrophotometer according to claim 2, further comprising a motor to rotate said at least one mirror.

4. The spectrophotometer according to claim 3, further comprising a transducer to provide a signal for said means for operating said diodes in at least one angular position of said at least one mirror, said motor being a stepping motor, the control input of which is connected to said means for operating said diodes.

5. The spectrophotometer according to claim 3, further comprising a transducer to provide a signal corresponding to the current angular position of said at least one mirror for said means for operating said diodes, and said motor rotating said at least one mirror continuously.

6. The spectrophotometer according to claim 1, wherein said means for operating said diodes and said data processing unit are comprised by a microprocessor.

7. The spectrophotometer according to claim 1, wherein at least some of the radiation emitting diodes are provided with filters.

* * * * *